United States Patent
Tankovich

(10) Patent No.: US 10,973,757 B2
(45) Date of Patent: Apr. 13, 2021

(54) BIODEGARDABLE MICRONEEDLE DEVICE

(71) Applicant: Nikolai Tankovich, San Diego, CA (US)

(72) Inventor: Nikolai Tankovich, San Diego, CA (US)

(73) Assignee: StemProtein, LLC, San Diego, CA (US)

( * ) Notice: Subject to any disclaimer, the term of this patent is extended or adjusted under 35 U.S.C. 154(b) by 0 days.

(21) Appl. No.: 14/507,711

(22) Filed: Oct. 6, 2014

(65) Prior Publication Data
US 2016/0287668 A1 Oct. 6, 2016

(51) Int. Cl.
A61M 39/00 (2006.01)
A61K 9/00 (2006.01)
A61M 37/00 (2006.01)

(52) U.S. Cl.
CPC ....... *A61K 9/0021* (2013.01); *A61M 37/0015* (2013.01); *A61M 2037/0023* (2013.01); *A61M 2037/0046* (2013.01); *A61M 2037/0053* (2013.01)

(58) Field of Classification Search
CPC ............ A61K 9/0021; A61M 37/0015; A61M 2037/0023; A61M 2037/0046; A61M 2037/0053; A61M 2037/0061
See application file for complete search history.

(56) References Cited

U.S. PATENT DOCUMENTS

| | | | | |
|---|---|---|---|---|
| 2008/0268007 A1* | 10/2008 | Meng | ................... | A61K 8/0208 514/1.1 |
| 2008/0269685 A1* | 10/2008 | Singh | ................... | A61K 9/0021 604/173 |
| 2009/0234301 A1* | 9/2009 | Tomono | ............ | A61M 37/0015 604/272 |
| 2013/0072874 A1* | 3/2013 | Tokumoto | ......... | A61M 37/0015 604/173 |
| 2014/0371713 A1* | 12/2014 | Quan | ..................... | A61K 47/26 604/506 |

* cited by examiner

*Primary Examiner* — Nathan R Price
*Assistant Examiner* — Courtney B Fredrickson
(74) *Attorney, Agent, or Firm* — TMB Law; Timothy M. Brown

(57) ABSTRACT

A microneedle device for delivering therapeutic ingredients to the dermis or epidermis. The device contains biodegradable microneedles, which extend from a backing, and are sandwiched between a cap film and a film which is coextensive with the tips of the microneedles and the spaces on the backing between the microneedles.

11 Claims, 1 Drawing Sheet

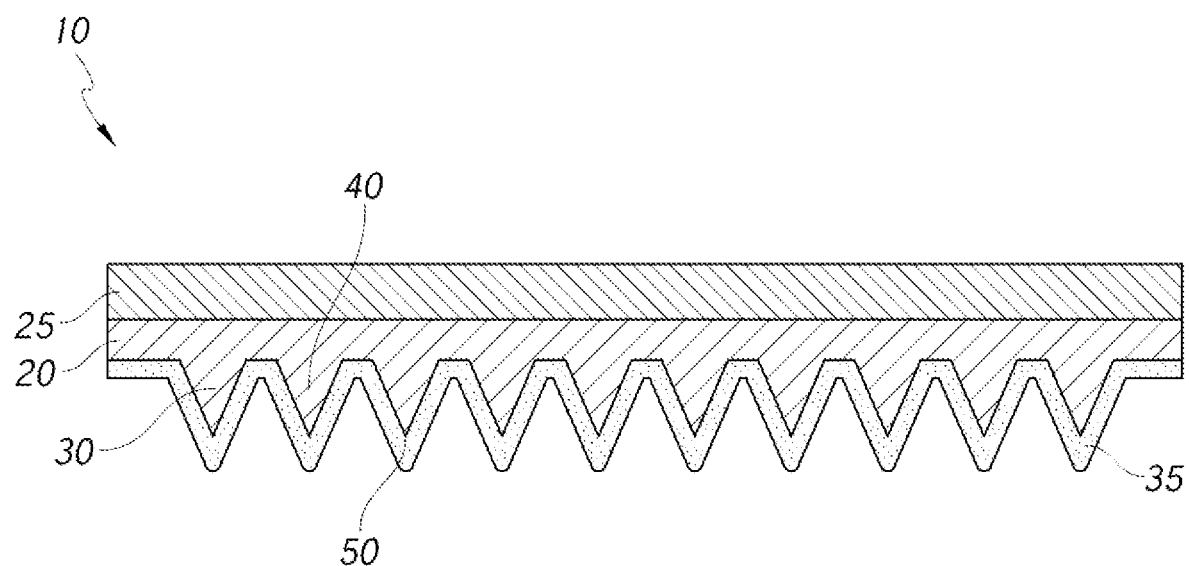

BIODEGARDABLE MICRONEEDLE DEVICE

FIELD OF THE INVENTION

The present invention relates to a microneedle device including a microneedle array provided with one or more biodegradable microneedles capable of piercing skin for administration of drugs to a living body. This invention is generally in the field of devices for the transport of therapeutic or biological molecules across tissue barriers, such as for drug delivery.

BACKGROUND

There is a large volume of published studies describing the role of the skin as a promising site for systemic delivery of active pharmaceutical ingredients (APIs). (Banga, 2006: Gupta and Sharma, 2009). Successful passive transdermal delivery is restricted to molecules sharing the following key properties of ideal skin permeant:low molecular weight of <500 Da; the demonstration of adequate lipophilicity with log partition coefficient preferably in the range of 1 to 3.5; potent molecules with typical daily dose of <10 mg and reasonable aqueous solubility of >100 µg/ml (Coulman et al., 2006a; Williams, 2003). This stems from the formidable barrier properties of the skin's stratum corneum (SC), also known as the horny layer. This uppermost layer of the skin consisting of corneocytes embedded in lipid-enriched matrix with a thickness of approximately 10-15 µm, is a key factor in regulating drug flux through the tissue (Wiechers, 1998; Williams, 2003).

Most APIs however, are rather hydrophilic, charged or of large molecular size, making them far from ideal skin permeants. Recent developments in transdermal drug delivery therefore have heightened the need for strategies to overcome the stratum corneum barrier function in order to facilitate rapid and effective permeation of a broader range of molecules, including macromolecular therapeutics and genetic materials. Such strategies to overcome the stratum corneum barrier properties namely via optimisation of the drug formulation or manipulation of the SC barrier function, can be achieved by one of two main approaches—either by chemical or physical methods.

Conventional transdermal delivery strategies, well established for small molecules, are focused on optimisation of drug formulation. For macromolecules such as protein/peptide drugs, optimisation of the formulation can be performed by encapsulation of macromolecules within vesicular carrier systems such as liposomes, chemical modification for synthesising more lipophilic analogues, or incorporation of chemical penetration enhancers and proteolytic enzymes inhibitors.

However, as this approach does not significantly disrupt the skin barrier, its application might be limited to only small peptides. Other transdermal enhancement technologies rely on manipulating the stratum corneum barrier properties by means of application of physical energy, or by physical abruption of the stratum corneum and, finally, by controlled removal of the stratum corneum so that permeation of drug molecules could be increased.

Recent and emerging progress in microneedle (MN) technologies are now used to disrupt the barrier properties of the SC, thus enabling enhanced transdermal drug delivery.

Microneedle (MN) Arrays

MN arrays consist of a plurality of micron-sized projections typically assembled on one side of a supporting base or patch. These microprojections generally range from lengths as short as 25 µm to those as long as 2,000 µm. The first concept for the use of MN as a drug delivery device was filed in 1971 in a United States patent in which the inventors, Gerstel and Place, used the term 'puncturing projections' to describe this invention (Gerstel and Place, 1976). However, the first serious discussions and proof-of-concept analyses of MN emerged in the late 1990s, when Henry et al. (1998) demonstrated the use of silicon MN to successfully facilitate the delivery of a model drug, calcein, across human skin.

A large and growing body of literature has investigated various microfabrication methodologies used to manufacture MN arrays from numerous materials. These materials have included silicon; metals such as stainless steel, palladium, nickel and titanium carbohydrates including galactose, maltose and polysaccharide, glass, ceramics and various polymers.

In addition, MN arrays have been produced in various different geometries. These microstructure geometries can be in the form of needle-like (most common MN geometries which can be sharp-, tapered-, conical- or bevel-tipped), microblades, blunt-projections or shaped in an arrow-head.

MNs have been shown to effectively enhance the delivery of many therapeutic molecules across biological membranes including skin, mucosal tissue and sclera. Upon application of MN arrays, transient micropores, orders of magnitude larger than the molecular dimensions of the target molecule are created.

In 2004, it was suggested that MN arrays could be used to permit the transport of, not only small molecular weight APIs but macromolecules and possibly supramolecular complexes and microparticles. MNs could allow for the easy and patient-friendly administration of therapeutics to and across the skin at low cost with potential efficacy as a parenteral route of administration.

Modulation of MN geometry and simple alteration of drug formulations can result in controlled drug deposition within targeted skin layers. MNs have been shown to penetrate the skin and cross the stratum corneum into the viable epidermis, avoiding contact with nerve fibers and blood vessels that reside primarily in the dermal layer. Therefore, the use of MNs would provide a pain-free, minimally invasive means of delivering both small and large molecular weight APIs with the prevention of bleeding at the application site.

Over the last decade, extensive research has been carried out concerning MN design with the use of a wide range of techniques and fabrication methods. Importantly, enhancement of the delivery of drugs and biomolecules of a wide variety of physicochemical properties has been demonstrated in in vitro, ex vivo and in vivo experiments, using a broad variety of device designs.

Microneedles

Biodegradable polymeric microneedles (MN) are micronscale solid structures that are embedded with active pharmaceutical ingredients as dissolvable MN patches.

MN patches are applied to the skin and penetrate into the dermis of the skin where they deposit active pharmaceutical ingredient.

Dissolvable polymeric MN patches are made of water-soluble biodegradable materials.

To date, dissolvable microneedle (MN) patches are prepared with water-based solutions of active pharmaceutical ingredient, polymers, and fillers in a process that involves simultaneous drying of the vaccine and formation of the MN, which requires optimal conditions for both. This approach is inherently limited in its ability to achieve long-term biopharmaceutical stability because water cannot be removed effectively during the drying process without increasing the drying temperature, which then damages the biological material.

SUMMARY

The device of the invention is embodied in the form of a microneedle for application to the skin. In general embodiments, the device has a cap made from a film which is a biocompatible polymer having upper and lower surfaces. Abutting the lower surface of the cap is a backing from which projects at least one biodegradable microneedle. The length of the microneedle projections extends from the lower surface of the backing and terminates in a tip distal from the lower surface of said backing. The microneedle projections are formed from a polymeric blend of preserved stem cell factors. Coextensively covering the microneedles and the lower surface of the backing is a film formed from a flexible biocompatible material. Upon applying the device to the skin with pressure upon the cap, a length of the microoneedles penetrates the film and the epidermis of the skin, thereby positioning the microneedle in the dermis, wherein the microneedle biodegrades and delivers said stem cell factors to the dermis. In various embodiments, the coextensive film does not comprise bioactive agents.

FIGURES

FIG. 1 is a cross section of an array of microneedles embodied in the device.

DETAILED DESCRIPTION

Definitions

Active Pharmaceutical Ingredient (API) is defined as biotherapeutic or biopharmaceuticals or biologicals or chemicals in drug products that make the medications work. In a therapeutic context, biologically engineered proteins, recombinant molecules and cell secreted products are considered APIs. API's are also referred to herein as 'agents' or "therapeutic agents."

"Array" refers to the medical devices described herein that include one or more structures capable of piercing the stratum corneum to facilitate the transdermal delivery of therapeutic agents. Arrays of microneedles are also referred to as microneedle patches.

"Microstructure," "microneedle" or "microarray" refers to the specific microscopic structures associated with the array that are capable of piercing the stratum corneum to facilitate the transdermal delivery of therapeutic agents. By way of example, microstructures can include needle or needle-like structures as well as other structures capable of piercing the stratum corneum.

As used herein, the term "stem cell" refers to an undifferentiated cell which has the ability to both self-renew (through mitotic cell division) and undergo differentiation to form a more specialized cell, Stem cells have varying degrees of potency. A precursor cell is but one example of a stem cell.

The term "mesenchymal cell" refers to mesodermal germ lineage cells which may or may not be differentiated. The mesenchymal cells of the invention include cells at all stages of differentiation beginning with multipotent mesenchymal stem cells, down to fully differentiated terminal cells.

The term "patient," or "subject," refers to animals, including mammals, preferably humans, who are treated with the pharmaceutical compositions or in accordance with the methods described herein.

The term "pharmaceutically acceptable carrier" (or medium), which may be used interchangeably with the term "biologically compatible carrier" (or medium), refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

As used herein, a "therapeutically effective amount," or "effective amount," refers to an amount of an API required to produce a therapeutic effect or improvement in the disorder (e.g. skin condition) that is being treated.

The term "stem cell composition" refers to a composition containing whole stem cells, stem cell factors, microvesicles, or a combination thereof.

The term "stem cell derivative" includes, but is not limited to, biomolecules, cellular vesicles (e.g. secretory vesicles), whole stem cells (live or dead), cell organelles, membranes, and combinations thereof.

The term "biomolecule" refers to any molecule produced by a living cell including, but not limited to, proteins, peptides, amino acids, fatty acids and fatty acid alcohols, sterols, nucleic acids (e.g. DNA and/or RNA) and combinations thereof.

As used herein, "treating" or "treat" includes (i) preventing a pathologic condition (e.g. skin condition) from occurring; (ii) inhibiting the pathologic condition (e.g. skin condition) or arresting its development; (iii) relieving the pathologic condition (e.g. skin condition), or (iv) alleviating the symptoms associated with the condition (e.g. skin condition).

The term "clone," or "clonal cell," refers to a single cell which is expanded to produce an isolated population of phenotypically similar cells (i.e. a "clonal cell population").

The term "cell line" refers to one or more generations of cells which are derived from a clonal cell.

The terms "administration" and "administering" as used herein refer to the delivery of a stem cell composition by an administration route including, but not limited to, intravenous, intra-arterial, intramuscular, intraperitoneal, subcutaneous, intramuscular, topically, or combinations thereof.

"Rejuvenating composition" refers to a composition that improves the appearance of, or rectifies, a condition (e.g. skin condition).

Dissolving Microneedle Fabrication Methods

Dissolving microneedles have been fabricated mostly using micromolds filled by solvent casting (with water as the usual solvent), filled with a polymer melt allowed to solidify in the mold, and in-situ polymerization of liquid monomer in the mold. Others have used methods of fabrication involving polymer/sugar melts and polymer/sugar solutions, chondroitin sulfate, dextran, dextrin, PVP, PVP, PLGA, fibroin and sugars, which have been dissolved in water, filled into the mold cavities and allowed to dry, sometimes with the additional use of vacuum and/or centrifugal force.

Dissolving microneedles completely dissolve in the skin. These microneedles are typically made solely of safe, inert, water-soluble materials, such as polymers and sugars that will dissolve in the skin after insertion. Drugs are often encapsulated inside the microneedle for release into the skin similarly to coated microneedles. The device of the present invention comprises dissolving microneedles.

Melted maltose has been filled in the cavities of a mold and solidified upon cooling. Using a related approach, N-vinylpyrrolidone and/or methacrylic acid were added as liquid monomers into a mold and polymerized under ultraviolet radiation. In contrast to these highly water-soluble, rapidly dissolving microneedles, polymeric microneedles designed for slow biodegradation in the skin have also been fabricated by micromolding polylactic acid, polyglycolic acid and their copolymers as melts using PDMS and silicon molds.

Another fabrication method draws up liquid formulations to form tapered microneedle structures that solidify in position. Maltose microneedles can be formed as multi-needle arrays using a controlled, stepwise drawing technique enabled by a microfabricated device. Microneedles made of dextrin, chondroitin sulfate and albumin are similarly fabricated one-by-one by drawing using pipette tips. An ultrasonic welding method can be used to form biodegradable polymer microneedles out of polymer particles welded together without bulk heating of the polymer, which resulting in minimal damage to encapsulated compounds.

Dissolving Microneedle Formulations and Designs

Heat-sensitive compounds like proteins and antigens are encapsulated in microneedles and solidified at moderate conditions that will not damage their activity. For example, dissolving microneedles can be fabricated out of hydrophilic polymers cast in an aqueous solution at room temperature and at atmospheric pressure or under vacuum.

Dissolving microneedles, depending on the formulation, can be formed such that upon insertion into skin they will dissolve in 5 minutes. Biodegradable polymer microneedles may be inserted and remain in the skin for at least several days to effectively utilize their controlled-release degradation properties to provide controlled-release delivery in skin for up to months.

Because microneedles may not insert fully into skin, it is sometimes desirable to encapsulate drugs only in the microneedle tips.

DESCRIPTION OF EMBODIMENTS

The present invention is a dissolvable, solid polymeric microneedle (MN), an embodiment of which is a microneedle patch for transdermal delivery of active pharmaceutical ingredients (API).

Where the microneedle devices are to be used for transdermal drug delivery, the height of the microneedles is preferably sufficient to pass through the stratum corneum and into the epidermis.

As used in connection with the present invention, the term "microneedle" (and variations thereof) refers to structures having a height projecting from the surface of the backing from which they protrude of about 500 micrometers or less. In some instances, microneedles of the present invention may have a height of about 250 micrometers or less.

Although the illustrative microneedle devices described herein all include multiple microneedles, it will be understood that microneedle devices of the present invention may include only one microneedle on each backing. Further, although the microneedle devices are all depicted with only one backing, each device could include multiple backings, with each backing including one or more microneedles protruding therefrom.

Referring now to FIG. 1, a portion of one microneedle device 10 is illustrated with microneedles 30 protruding from a surface of a microneedle backing 20. The microneedles may be arranged in any desired pattern or distributed over the backing surface randomly.

The microneedle comprises a first film 35 coextensively covering said microneedle and the surface of said backing between bases 40 of the microneedles. The film is formed from a flexible biocompatible material. In use, upon applying the device to the skin with pressure (e.g. finger or thumb pressure) upon the cap film 25, a length of the microneedle penetrates the film and the stratum corneum of the epidermis of the skin, which positions the tip and a length of the microneedle to depths as shallow as the basal layer of the epidermis, or deeper into the dermis. In the dermis, the microneedle biodegrades and delivers said stem cell factors to the dermis.

The first film includes two sides, one of which is oriented to face the tips of the MNs.

Each of the tips of the microneedles 30 upon finger pressure application to the cap film 25 causes the tips 50 of the microneedles to pierces through the first film 35 such that at least the tip and all or a portion of the height of the microneedle is located in the dermis.

The first film and the cap film may be formed from the same or from different liquid impermeable polymeric film material. One example of a suitable polymeric film may be, hydroxyl propyl cellulose (with a thickness of, e.g., about 10 to about 20 micrometers). Regardless of the material or materials used for the film structure, it may be a non-homogeneous structure, e.g., a multi-layer construction.

Although the depicted MN is in the form of circular cylindrical pillars, it should be understood that the MNs structure may be provided in any suitable shape or combination of shapes, e.g., pyramids, hemispherical protrusions, walls.

The film may preferably be largely coextensive with the surface of the backing from which the microneedles protrude.

Alternatively, the film may be provided in separated, discrete locations across the array of MNs.

In one respect the device is a thermostable, three-dimensional, dry formulation of SCFs, i.e. a dissolvable polymeric microneedle (MN) patch for transdermal delivery of thermostable SCF.

A step in the making of the three-dimensional formulation of SCFs comprises micronization of the SCF into a powder, and encapsulation of the SCF powder inside a polymer such that the polymeric MN patch of the invention is embedded with SCF powder.

Accordingly, the device of the invention is a dissolvable polymeric MN patch embedded with dry thermostable SCF powder, preferably ambient temperature-stable SCF for delivery through the skin without a requirement for reconstituting the thermostable SCF formulation, The bioactive SCF is preserved in a dry state and stable at ambient temperatures.

Method of Preparing Stem Cell Factor (SCF) Composition

A preferred method of preparing dry, micronizable, thermostable SCF is preservation by vaporization (PBV). Incorporated herein by reference, US Publ. No. 2012 014 1433 provides guidance for preparation of a stem cell derivative composition, also referred to herein as a composition of stem cell factors (SCF). Using PBV technology, dry thermostable stem cell derivative compositions are produced, which are then formed into micronized powder and incorporated into MN devices of the invention for delivery of SCF to the dermis.

In some aspects, the stem cell derivative comprises at least one stem cell factor. As used herein, the term "stem cell factor" refers to cellular molecules which influence the growth, proliferation, commitment, and differentiation, for example, of other cells (e.g. stem cells) either in vivo or in vitro. Stem cell factors include, but are in no way limited to, cytokines, growth factors, common beta chain, common gamma chain, and IL-6 cytokine families, adrenomedullin, insulin-like growth factor, epidermal growth factor EGF, fibroblast growth factor FGF, autocrin motility factor, GDF, IGF, PDGF, vascular endothelial growth factor (VEGF (e.g. VEGFA)), growth differentiation factor 9, erythropoietin, activins, TGF-α, TGF-β, bone morphogenetic proteins (BMPs), Hedgehog molecules, Wnt-related molecules, and combinations thereof.

In use, the MN patch of the invention is applied to the skin for penetration into the superficial dermal and/or epidermal layers of the skin where they deposit SCFs.

The MN itself comprises dissolvable polymeric MN patches made of water-soluble biodegradable materials.

Preserving Stability of Biomolecules

Many conventional pharmaceuticals are stored at ambient temperatures and delivered via oral, transdermal, respiratory, and uro-genital routes without reconstitution with water prior to delivery, thereby avoiding painful needle-based delivery and trained medical personnel. The pharmaceutical industry has developed sophisticated methods and tools for needle-free delivery of conventional pharmaceuticals, including tablets, dissolvable films, patches, suppositories, and ointments. However, production of these needle-free delivery devices often requires the use of materials and conditions that could be damaging to the biological activity of fragile biologicals, such as vaccines, including short-term application of high temperatures, shear stresses, and damaging chemicals. This presents a challenge for developing needle-free delivery devices for active biopharmaceuticals. Furthermore, unlike conventional pharmaceuticals, biopharmaceuticals are not stable at ambient temperatures.

Most thermolabile, fragile biopharmaceuticals or biomolecules are currently preserved in the dry state using freeze-drying (FD) or spray-drying (SD) technology. However, most biopharmaceuticals produced using FD and SD are not thermostable, and cannot be used for needle-free vaccine delivery. FD and SD technologies have failed to deliver thermostable vaccines that can be stored at ambient temperatures long-term (many months) because of fundamental physical limitations. In this proposal we will use our novel PBV technology platform, which allows production of dry thermostable vaccines that can be micronized into powder and incorporated into needle-free vaccine delivery devices (e.g., dissolvable tablets, films, and patches), and retain biological activity.

On the other hand, a number of studies have demonstrated that evaporative drying from thin films can produce very thermostable vaccines and other biopharmaceuticals (Bronshtein V, Frank J L, Leopold A C (1996) Protection of desiccated enzymes by sugars. 33rd Annual Meeting of the Society for Cryobiology. Indianapolis, Ind.; Bronshtein V, Leopold A C (1996) Accelerated aging of dried luciferase and isocitrate dehydrogenase. Effect of sugar/enzyme mass ratio. 33rd Annual Meeting of the Society for Cryobiology. Indianapolis, Ind.). However, drying from thin films is difficult to scale and cannot be used to produce thermostable vaccines for needle-free delivery devices, such as respiratory devices, dissolvable films, patches, etc. The process of foam drying was introduced to scale-up evaporative drying from thin films and has been used to successfully preserve a variety of proteins and live viral and bacterial vaccines (Abdul-Fattah A M, Truong-Le V, Yee L, Nguyen L, Kalonia D S, et al. (2007) Drying-induced variations in physico-chemical properties of amorphous pharmaceuticals and their impact on stability (I): stability of a monoclonal antibody. J Pharm Sci 96: 1983-2008; Abdul-Fattah A M, Truong-Le V, Yee L, Pan E, Ao Y, et al. (2007) Drying-induced variations in physico-chemical properties of amorphous pharmaceuticals and their impact on Stability II: stability of a vaccine. Pharm Res 24: 715-727; Bronshtein V (2004) Preservation by Foam Formulation: An Alternative to Freeze-Drying. Pharmaceutical Technology 28: 88-91; Hajare A A, More H N, Pisal S S (2011) Effect of sugar additives on stability of human serum albumin during vacuum foam drying and storage. Curr Drug Deliv 8: 678-690; Ohtake S, Martin R, Saxena A, Pham B, Chiueh G, et al. (2011) Room temperature stabilization of oral, live attenuated *Salmonella enterica* serovar *Typhi*-vectored vaccines. Vaccine 29: 2761-2771; Ohtake S, Martin R A, Saxena A, Lechuga-Ballesteros D, Santiago A E, et al. (2011) Formulation and stabilization of *Francisella tularensis* live vaccine strain. J Pharm Sci 100: 3076-3087; Pisal S, Wawde G, Salvankar S, Lade S, Kadam S (2006) Vacuum foam drying for preservation of LaSota virus: effect of additives. AAPS PharmSciTech 7:60.

Using foam-drying methods, for example but not by way of limitation, Preservation by Vaporization (PBV), eliminates splashing and other drawbacks of prior foam drying methods. Bronshtein V (2005) Preservation by Vaporization.

PBV is comprised of primary drying of biological material under vacuum by vaporization (simultaneous sublimation, boiling, and evaporation) from a partially frozen (i.e. slush) state at near subzero temperatures. After the primary drying stage, stability-drying is carried out at elevated temperatures (i.e. above 40° C.). PBV can be performed in unit dose format (in vials) and/or aseptically in bulk format (in trays, bags, or other containers). PBV drying can be performed using conventional freeze- or PBV can be used to perform continuous load barrier drying in an industrial scale manifold vacuum dryer format. PBV has been used to successfully preserve fragile biologicals with higher activity immediately after drying (i.e. initial yield), short-term stability at high temperatures (60–90° C.), and long-term stability at ambient temperatures (25° C., 37° C., and higher). PBV-preserved biopharmaceuticals can also be micronized to produce powders with particle size of 20 microns or lower. PBV enables not only long-term storage at ambient temperatures, but also short-term stability at high-temperatures not achievable by FD or SD. Using PBV, polymeric film preparations and three dimensional configurations (microneedles) comprising fragile biopharmaceuticals are achieved, which have thermostability.

Preparation of Stem Cell Factor (SCF) Composition

Preparation of an SCF composition, the active biological (API) component of the invention involves foam drying technology, referred to herein as Preservation by Vaporization (PBV). Preparation of mesenchymal stem cells, from which the SCF composition is derived, and PBV methods of dry preservation of SCF activity, is described in US Patent Publication No. 2012 014 1433 (incorporated herein by reference).

Preservation of SCF Bioactivity

PBV is comprised of the steps of primary drying of biological material under vacuum by vaporization (simultaneous sublimation, boiling, and evaporation) from a partially frozen (i.e. slush) state at near subzero temperatures. The method for formulating dissolvable polymeric microneedle patch devices involves formulating micronized sugar glass particles comprising thermostable SCF and embedded in dissolvable polymeric microneedles.

Thermostability of SCF in a dry state required to formulate SCF as microneedles such that devices of the invention will comprises SCF that will be stable (i.e. activity will be retained) long-term at ambient temperatures PBV involves a primary drying stage, followed by stability-drying at elevated temperatures (i.e. above 40° C.).

The microneedles of the invention involve an anhydrous method of preparing three-dimensional needles comprised of quick-dissolving polymers embedded with PBV-preserved biologicals (e.g. SCFs) for formulation of dissolvable microneedle (MN) patches.

A first stage of making the MNs of the invention involves stabilizing SCFs in dry sugar glass particles in the form of micronized powder, which is then incorporated into the MN without redissolving the particles. The stage of drying the SCFs is separate from the formation of three-dimensional microneedles comprising polymeric SCFs. In other words, the SCFs are dried under the optimal conditions for thermostabilizaton, and then incorporated into the MNs using an anhydrous solvent, such that the SCF remains in the dry and stabilized state throughout the process of making MNs or MN patches.

Accordingly, the SCF embedded in a thermostable dry state into the MN is stable after storage for 1 year at 25° C. and 37° C., i.e. stabile in the patch embodiment at ambient temperatures.

Micronization of PBV

SCF composition is preserved in the form of a micronized powder. The powder is encapsulated in a biodegradable polymer which results in minimal damage to survival of SCF biological activity.

PBV-preserved SCF foam was micronized with a ball mill into powder with a particle size of <20 microns. Micronized PBV-preserved SCF powder was incorporated into an anhydrous polymer mixture, and quick-dissolving polymer formulations were formulated in molds.

Fabricating Microneedles

For the present invention, an anhydrous method of preparing quick-dissolving films embedded with PBV-preserved biologicals is used for formulation of dissolvable microneedle (MN) patches.

Stem Cell Factor Composition was first stabilized in dry sugar glass particles and then incorporated into the MN without redissolving the particles. By separating the drying of the vaccine from the formation of MNs, the SCF composition can be dried under the optimal conditions and then incorporated into the MNs using an anhydrous solvent, such that the SCF remains in the dry and stabilized state throughout the process of making MN patches. Accordingly, dissolvable polymeric MN patches are prepared, the biodegradable microneedles of which encapsulate an appropriate dose of the active pharmaceutical ingredient(s) (e.g. stem cell factors) in the MN without compromising the activity or stability of the encapsulated SCF powder.

Polymer Choice—Considerations

In the dissolving MN system of delivery, the rates at which constituent polymers dissolve within the skin will influence the release kinetics of the incorporated drug. To this end, careful consideration when selecting the polymer of choice from which to fabricate the MN arrays plays an important role in dictating the dissolution characteristics of the drug in question. Controlled drug delivery is achievable by adjustment of the polymeric composition of the MN array or by modification of the MN fabrication process.

Preparation of Dissolvable Polymeric Microneedle Patches

Without limiting the methods of making MN disclosed herein, the following references provide teachings for employing other methods and materials, all of which are included in embodiments of the present invention. Dissolving MNs are fabricated primarily from polymers mainly due to the biocompatibility, biodegradability and long established safety profiles of polymers in medical tools (Park et al., 2005, 2007; Jin et al., 2009). Examples of polymers used in the fabrication of dissolving MNs include polylactic acid (PLA) (Aoyagi et al., 2008; Park et al., 2005), polyglycolic acid (PGA), polylactic-co-glycolic acid (PLGA) (Park et al., 2005), polyvinylpyrrolidone (PVP), poly(vinylpyrrolidone-co-methacrylic acid) (PVP-MAA) (Sullivan et al., 2008) and poly(methyl vinyl ether-maleic anhydride) (Donnelly et al., (2010). Biopolymers such as sodium hyaluronate (Matsuo et al., 2012a, 2012b), chondroitin sulphate (Ito et al., 2011, Naito et al., 2012) and carbohydrates e.g. sugars, carboxymethyl cellulose and amylopectin (Lee et al., 2008; Park et al., 2010) have also been employed, and useful in fabricating embodiments of the present invention.

MicroMolding

By way of example but not limitation, a male metal MN master-mold (A) with specifications based on Lee et al. 2008 Biomaterials 29:2113-212 has MNs which are pyramidal or conical in shape, 600 µm long, 300 µm wide at the base, and 25 µm wide at the tip; the density of MNs is 100 MNs per square centimeter with a total of 100 MNs per patch.

Female silicone (PDMS) production molds (B) were prepared from the master-mold. Polymeric patches were prepared using a solvent casting method adapted from preparation of polymeric films. Anhydrous solutions of polymers, e.g. polymers used in the fabrication of dissolving MNs include polylactic acid (PLA), polyglycolic acid (PGA), polylactic-co-glycolic acid (PLGA), polyvinylpyrrolidone (PVP), poly(vinylpyrrolidone-co-methacrylic acid) (PVP-MAA) and methyl vinyl ether-maleic anhydride). Biopolymers such as sodium hyaluronate, chondroitin sulphate, and carbohydrates e.g. sugars, carboxymethyl cellulose, polyvinyl chloride and amylopectin of varying molecular weights (80 kDa to 370 kDa) were used to produce patches with different mechanical characteristics.

An alternate method of making the microneedles and MN arrays of the invention is adapted from U.S. Pat. No. 8,101,114, incorporated by reference. This method avoids the high temperatures and pressures of traditional processing which can be detrimental to molding materials and the biotherapeutic agents within. Microneedle arrays are formed by particle based molding 140. Micromolds are fabricated and filled with particles. Energy (e.g. ultrasound) is applied to the micromold containing the particles resulting in creation of a microneedle structures in the micromold.

A variety of mold-based techniques were employed in the production of dissolving MNs including solvent casting (Mansoor et al., 2012), modified thermal imprinting (Shibata et al., 2011), hot embossing (Han et al., 2007), laser machining (Aoyagi et al., 2007; Donnelly et al., 2011), micro-injection molding (Wang et al., 2008) and polymer investment moulding (Lippmann et al., 2007).

Criteria for Fabrication of Dissolving Microneedles

Microneedles for self-administration of biotherapeutics from a MN patch are preferably prepared with: (1) gentle fabrication to avoid damaging sensitive biomolecules, (2) sufficient mechanical strength for insertion into skin, (3) controlled release for bolus and sustained drug delivery, and (4) rapid dissolution of microneedles made of safe materials.

Polymer Microneedles

Alternative methods may be used in making biodegradable polymeric microneedles. In one method, polymeric microneedles are made using microfabricated molds. For example, the epoxy molds can be made as described below and injection molding techniques can be applied to form the microneedles in the molds (Weber, et al., "Micromolding—a powerful tool for the large scale production of precise microstructures", Proc. SPIE—International Soc. Optical Engineer. 2879, 156-167 (1996); Schift, et al., "Fabrication of replicated high precision insert elements for micro-optical bench arrangements" Proc. SPIE—International Soc. Optical Engineer. 3513, 122-134 (1998) (U.S. Pat. No. 8,708,966 incorporated by reference).

FILMS (Coatings) (Also See Gill and Prausnitz: Coated MNs for Transdermal Delivery)

A variety of methods are known for coating microneedle arrays. In a method of coating a microneedle array adapted from U.S. Pat. No. 8,057,842 (incorporated herein by reference), a coating fluid is applied using a flexible film in a brush-like manner using a device disclosed in the '842 patent. The method involves coating a flexible film with a coating solution comprising a carrier fluid and a coating material. The coating solution (a carrier fluid and a coating material) is applied to a surface of the flexible film. In transferring the coating of the film to a surface of the microneedle array, a transfer step brings the surface of the flexible film into contact with a desired surface of the microneedle array, the film is removed from contact with the chosen surface of the microneedle array; then removing the flexible film from contact with the microneedles array, finally allowing the carrier fluid to evaporate. The method allows one to select which surface(s) of the MN array to apply a dried coating deposited from a coating fluid; the thickness of the coating, the location can be adjusted and controlled.

Another method of coating a surface of a microneedle array is detailed U.S. Pat. No. 8,771,781 (incorporated by reference). This method employs the use of mask plates for applying coatings (films) to desired locations on a microneedle array. The coating solutions are filled on flat mask plate having blind holes as apertures arranged in rows and columns. The apertures are filled to a specified capacity with the coating solution. Microneedles are inserted in in the apertures filled with the coating solution to coat the microneedles. The substrate surface between microneedles may also be coated in a subsequent step with a mask with apertures patterned for depositing coating to the surface of the substrate between the needles. The surface on the opposite side of the substrate may be coated as well in a step coordinated with the coating of the microneedles themselves and the substrate surface between the miccroneedles.

PBV Preservation, Micronization, and Formulation of Microneedle (MN) Patches.

A process was developed for preparing MN patch devices using micronized sugar glass particles containing thermostable SCF. Micronized sugar glass particles (containing PBV-SCF) are about 10 μm in size, small enough to fill in the MN mold cavities. Other groups currently produce MN patches with vaccines formulated in aqueous solutions containing stabilizing excipients (Sullivan S P, Koutsonanos D G, Del Pilar Martin M, Lee J W, Zarnitsyn V, et al. (2010) Dissolving polymer microneedle patches for influenza vaccination. Nat Med 16: 915-920).

However, because the sugar glass particles are water-soluble, the casting solution needs to be formulated using a non-aqueous solvent, i.e. compatible organic solvents and plasticizers with PBV-preserved SCFs biologics for preparation of dissolvable films and patches.

Accordingly, solvent casting was used to produce quick-dissolving films in the needle-like form containing micronized PBV-preserved SCFs. These mixtures are used for preparing MN patches with sugar-glass particles.

To determine patch-fill volume, dry sugar glass particles containing SCFs were added into the cavities of the female PDMS production mold. Excess particles were removed using a micro-vacuum technique to ensure that particles only line the inside of the cavities.

Next, a casting solution is used to fill the MN cavities in the female production mold by spin-casting in a centrifuge (Bediz B, Korkmaz E, Khilwani R, Donahue C, Erdos G, et al. (2013) Dissolvable Microneedle Arrays for Intradermal Delivery of Biologics: Fabrication and Application. Pharm Res.; DeMuth P C, Min Y, Huang B, Kramer J A, Miller A D, et al. (2013) Polymer multilayer tattooing for enhanced DNA vaccination. Nat Mater 12: 367-376; Lee J W, Park J H, Prausnitz M R (2008) Dissolving microneedles for transdermal drug delivery. Biomaterials 29: 2113-2124; Raphael A P, Prow T W, Crichton M L, Chen X, Fernando G J, et al. (2010) Targeted, needle-free vaccinations in skin using multilayered, densely-packed dissolving microprojection arrays. Small 6: 1785-1793).

Finally, the molds are allowed to dry in a chemical hood, thereby creating MNs embedded with sugar glass particles.

Polymeric microneedle patches embedded with SCFs have thermostability in the patch formulation Micronization of sugar glass SCF was carried out with a ball mill using a previously optimized process to achieve a particle size of about 10 μm. Micronization was performed in a dry room, and the particle size distribution in the milled specimens is measured with Malvern Mastersizer M2000.

Molding of MN patches embedded with micronized SCF powder (which has been stored in sealed vials at 25° C. in the dry room) was achieved as described herein.

Once the MN patches are dry, they will be removed from the molds, sealed in sterile aluminum pouches containing desiccant to control humidity, and placed at 25° C. and 37° C. for stability testing. Immediately after incorporation into MN patches, SCF activity is measured with a standard assay, e.g. VEGF assay, and the mechanical properties of the vaccine MN patches will also be evaluated.

Polymeric MN patches embedded with dry preserved SCF powder are formed containing standard human doses as determined by the methods of Lee et al. (Biomaterials 2008 29(13): 2113-2124.

Real-time stability evaluation of dry preserved SCF within MN patches includes at least 4 months of storage at 25° C. and 37° C.

The Delivery of Therapeutic and Model Compounds Using Dissolving Microneedles

The major advantages of biocompatible and biodegradable polymeric MN systems include loading a drug to be delivered into the MN matrix for release in skin interstitial fluid. Microneedle devices suitable for use in the present invention may be used to deliver therapeutic agents or drugs (including any pharmacological agent or agents) through the skin in a variation on transdermal delivery, or to the skin for intradermal or topical treatment.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants.

By way of example but not limitation, active pharmaceutical ingredients which are suitable for delivery by the microneedle of the present invention for dermatological treatments include minoxidil (typically to stimulate hair growth and to slow balding), retinoic acid compositions (for treatment of aging (e.g. photoaging) skin treatment of wrinkles), and botulinum toxin (BOTOX®) improve the look of both moderate to severe crow's feet lines and frown lines between the eyebrows and moderate to severe crow's feet lines in adults.

Another set of embodiments includes microneedles in which the biodegradable polymeric blend comprises one or more groups of therapeutic agents consisting of preserved stem cell composition or stem cell derivative, biomolecules, and one or more active pharmaceutical ingredients.

Guidance for selection of agents for treating pathologic skin is found in Women's Dermatology, edited by Lawrence Charles Parish, Sarah Brenner, and Marcia Ramos-e-Silva, Parthenon Publishing 2001. Guidance in formulation and administration of agents for treating dermatological conditions can be found in Chemistry and Technology of the Cosmetics and Toiletries Industry, edited by D. F. Williams (Springer Science and Business Media); Transcutaneous Drug Delivery System by Premjeet Sandhu (Editor), Piyush Trivedi (Editor), Bhupinder Singh, publ Publisher: AV Akademikerverlag GmbH & Co. KG. (2012); Microneedle-based drug delivery systems: microfabrication, drug delivery, and safety, Donnelly R F, Raj Singh T R, Woolfson A D. *Drug Deliv.* 2010 May; 17(4):187-207; Pierre M B, Rossetti F C Microneedle-based drug delivery systems for transdermal route, *Curr Drug Targets.* 2014 March; 15(3):281-91; Microneedles: an emerging transdermal drug delivery system, Shital H. Bariya, Mukesh C. Gohel, Om Prakash Sharma, Journal of Pharmacy and Pharmacology, Volume 64, Issue 1, pages 11-29, January 2012; Microneedle Integrated Transdermal Patch for Fast Onset and Sustained Delivery of Lidocaine, Jaspreet Singh Kochhar, Wan Xuan Selina Lim, Shui Zou, Wei Yan Foo, Jing Pan, and Lifeng Kang, Mol. Pharmaceutics, 2013, 10 (11), pp 4272-4280.

Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccine, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in United States Patent Application Publication No. 2004/0049150, the disclosure of which is hereby incorporated by reference.

Microneedle devices may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

Delivery Strategies

Micronneedles that dissolve or degrade have been used for delivery of therapeutics across the skin. Dissolving MNs function by creating microporation in the skin, followed by the dissolution of the MNs upon contact with the skin interstitial fluid. The drug payload of the MN matrix is then released over time.

Medical and Cosmetic Uses of the Invention

In some aspects, the invention finds use in medical and cosmetic applications for improving the health and appearance of the skin. Thus, the invention finds use in the treatment of degenerative skin conditions due to aging including, but not limited to, loss of skin elasticity (e.g. elastosis, solar elastosis, wrinkles and lines), loss of skin pigmentation (e.g. hypopigmentation, liver spots and lentigos), loss of skin turgor and decreased skin thickness.

The term "skin condition" also refers to disorders of the skin including, but not limited to, degenerative skin condition, skin disease, skin problems, which include, but are not limited, acne, eczema, psoriasis, rosacea, vitiligo, leucoderma, skin cancer, skin burns, skin allergies, congenital skin disorders, acantholysis, acanthosis, acanthosis nigricans, dermatosis, disease, erythroderma, furunculosis, impetigo, jungle rot, keratoderma, keratodermia, keratonosis, keratosis, keratosis nigricans, leukoderma, lichen, livedo, lupus, melanism, melanosis, molluscum, necrobiosis lipoidica, necrobiosis lipoidica diabeticorum, pemphigus, prurigo, rhagades, Saint Anthony's fire, seborrhea, vitiligo, xanthoma, xanthosis, Psoriatic arthritis, Reiter's syndrome, Guttate psoriasis, Dyshidriotic eczema, Acute and chronic graft versus host disease, Systemic sclerosis, Morphea, Spongiotic dermatitis, Allergic dermatitis, Nummular eczema, Pityriasis rosacea, Pityriasis rubra pilaris, Pemphigus erythematosus, Pemphigus vulgaris, Lichenoid keratosis, Lichenoid nitidus, Lichen planus, Lichenoid dermatitis, Seborrheic dermatitis, Autosensitization dermatitis, Dennatitis herpetiformis, and Eosinophilic dermatitis. In one specific embodiment, the skin disorder can be mediated by an immunological response. In another specific embodiment, the skin disorder can be a lymphocyte-mediated skin disorder. In another specific embodiment, the skin disorder can be selected from the group of alopecia greata, psoriasis, atopic dermatitis, lupus erythematosis, bullous pemphigoid, and psoriatic plaque. In another specific embodiment, the skin disorder can be psoriasis. In another specific embodiment, the skin disorder can be a chronic skin disorder. In another specific embodiment, the skin disorder can be an autoimmune skin disorder. In another specific embodiment, the skin disorder can be a malignant lymphoid disease that manifests in the skin.

The invention may also be applied in the treatment of injuries to the skin. That is, the invention may be used to improve the cosmetic appearance of, for example, scars, including burns (e.g. chemical and thermal burns). The invention also finds application in the treatment of vascular disorders of the skin such as varicose veins, chronic (long-term) venous insufficiency, thrombophlebitis, and arteriovenous fistula.

Use of the micronnedle invention herein is practiced by administering a stem cell composition to a patient suffering from a skin condition. As used herein, the terms "administering," "administered" and "administer" refer to any administration route by which a stem cell composition can be administered to a patient for a therapeutic effect as disclosed herein. In a preferred embodiment, the stem cell composition is administered may be administered locally. For example, elastosis may be treated by topically placement of the microneedle on the indicated area of skin, applying pressure to the cap thereby inserting the microneedle comprising a stem cell factor composition to the dermis underlying the selected area where a cosmetic improvement in the skin is desired.

The stem cell factor composition of the microneedle is a preserved composition. As used herein, the term "preserved" refers to the preservation of a material (e.g. stem cell derivative) by any of the methods disclosed in U.S. Publication No. 2008-0229609, the entire contents of which are incorporated herein by reference. Such processes include, but are not limited to, preservation by evaporation, freeze drying, secondary freeze drying, preservation by foam formation, vaporization, and combinations thereof.

As used herein, the term "vaporization" refers to a movement of molecules into a gas phase by evaporation, sublimation, or boiling.

Preservation by vaporization" (PBV) is a preservation process that comprises primary drying and stability drying, Primary drying is performed by intensive vaporization (sublimation, boiling and evaporation) of water at temperatures significantly (approximately 10° C. or more) higher than Tg' from a partially frozen and at the same time overheated (vacuum pressure is below the equilibrium pressure of water vapor) material.

In addition, unlike preservation by foam formation (PFF), preservation by vaporization (PBV) can be very effective for preserving biologicals contained or incorporated within an alginate gel formulation and other gel formulations. A PBV process can be performed by drying frozen gel particles under a vacuum at small negative (on the Celsius scale) temperatures. For such hydrogel systems, vaporization comprises simultaneous sublimation of ice crystals, boiling of water inside unfrozen microinclusions, and evaporation from the gel surface.

It should be noted that preserved stem cell derivatives include such derivatives in dry (e.g. containing less than 10% water by weight) and reconstituted form. For example, preserved stem cell derivatives include vaporized or lyophilized stem cell derivatives which have been reconstituted in an solution (e.g. pharmaceutically acceptable carrier) for administration to a patient.

In an exemplary, non-limiting embodiment of the invention, a skin disorder in a patient, such as elastiosis, is treated by topically administering to the patient the microneedle device of the present invention which comprises a vaporized stem cell derivative that comprises a therapeutic amount of at least one stem cell factor, including VEGF.

In such an embodiment, the stem cell derivative may be obtained from medium that has been conditioned by the growth of mesenchymal stem cells under low oxygen conditions. Such conditioned medium may be collected, concentrated, and then preserved by vaporization. The vaporized preserved conditioned medium, containing VEGF, may then be stored for a prolonged period of time before being reconstituted in a polymeric biodegradable composition in the form of a microneedle in the treatment or rejuvenation of the skin.

In a further embodiment, the coextensive film 35 may be formed from fast-drying polymers that create thin films after solvent evaporates. In commerce, these films are commonly found in 'liquid bandages' for wound care. Common varieties of such polymers include poly-vinyl-pyrrolidone PVP (water soluble), pyroxylin/nitrocellulose (alcohol soluble), and acrylate or siloxane polymers (isooctane soluble). For example "3M Cavilon No-Sting Barrier Film" contains no water, and includes these ingredients:

Iso-octane as a solvent
Poly-phenyl-methyl-siloxane copolymer, CAS 73559-47-4
Hexa-methyl-di-siloxane, CAS 107-46-0
Acrylate ter-polymer (3M trade secret)

In certain embodiments, 3M Cavilon is sprayed onto the microneedles to form a coat, that is, embodies the coextensive film 35. Such microneedles with acrylate/siloxane film repel water.

Further guidance in the pharmacokinetics and development of specific formulations delivering peptides, proteins, small molecules and vaccines by microneedle devices of the present invention is found in Erythropoietin-Coated ZP-Microneedle Transdermal System: Preclinical Formulation, Stability, and Delivery, Elaine E. Peters & Mahmoud Ameri & Xiaomei Wang & Yuh-Fun Maa & Peter E. Daddona Pharmaceutical Research 2012; Parathyroid Hormone (1-34)—Coated Microneedle Patch System: Clinical Pharmacokinetics and Pharmacodynamics for Treatment of Osteoporosis. Peter E Daddona, James A. Matriano, Jaap Mandema, Yuh-Fun Maa Pharmaceutical Research 2010; Effect of transdermal teriparatide administration on bone mineral density in postmenopausal women. E. Lane, Michael A. Bolognese, Jose R. Zanchetta, Pedro A. Garcia-Hernandez, Karen Sees, James A. Matriano, Kim Gaumer, Peter E. Daddona. Journal of Clinical Endocrinolology & Metabolism. 95:151-58, 2010; Demonstrated Solid-State Stability of Parathyroid Hormone PTH (1-34) Coated on a Novel Transdermal Microprojection Delivery System. Mahmoud Ameri, Peter E. Daddona, Yuh-Fun Maa. Pharmaceutical Research 2454-2463, 2009; Parathyroid Hormone PTH (1-34) Formulation that Enables Uniform Coating on a Novel Transdermal Microprojection Delivery System. Mahmoud Ameri, Shelley C. Fan, Yuh-Fun Maa. Pharmaceutical Research 27, 303-313, 2010; Effect of irradiation on parathyroid hormone PTH (1-34) coated on a novel transdermal microprojection delivery system to produce a sterile product—adhesive compatibility. Mahmoud Ameri, Xiaomei Wang, Yuh-Fun Maa. Journal of Pharmaceutical Science 99, 2123-34, 2010; Effect of delivery parameters on immunization to ovalbumin following intracutaneous administration by a coated microneedle array patch system Georg Widera, Juanita Johnson, Lomi Kim, Luz Libiran, Kofi Nyam, Peter E. Daddona, Michel Cormier, Vaccine 24, 1653-1664, 2006; Transdermal delivery of desmopressin using a coated microneedle array patch system Michel Cormier, Bonny Johnson, Mamoud Ameri, Kofi Nyam, Luz Libiran, Dee Dee Zhang and Pete Daddona, Journal of Controlled Release, 97, 503-511, 2004; Transdermal delivery of Antisense Oligonucleotides WeiQi Lin, Michel Cormier, and Peter E. Daddona, Celluar Drug Delivery: Principles and Practice, Humana Press, 227-285; Transdermal Drug Delivery Brad Phipps, Michel Cormier, Bob Gale, Bill van Osdal, Jay Audett, Rama Padmanabhan and Peter Daddona, Encyclopedia of Biomaterials and Biomedical Engineering, Marcel Dekker, Inc. New York, 1677-1689, 2004; Macroflux® Transdermal Technology Development for the Delivery of Therapeutic Peptides & Proteins Pete Daddona, PhD, Drug Delivery Technology 2, 54-57, 2002; Macroflux® Microprojection Array Patch Technology: A New and Efficient Approach for Intracutaneous Immunization James A. Matriano, Michel Cormier, Juanita Johnson, Wendy A. Young, Margaret Buttery, Kofi Nyam, and Peter E. Daddona, Pharmaceutical Research, Vol 19, 63-70, 2002; Macroflux® Technology for Transdermal Delivery of Therapeutic Proteins and Vaccines Michel Cormier and Peter E Daddona, Modified-Release Drug Delivery Technology, Marcel Dekker, Inc. New York, 589-598, 2002; Transdermal delivery of Antisense Oligonucleotides with Microprojection Patch (Macroflux®) Technology WeiQi Lin, Michel Cormier, Amad Samiee, Angie Griffin, Bonny Johnson, Ching-Leou Teng, Gregory E. Hardee and Peter E. Daddona, Pharmaceutical Research, 19, 1789-1793, 2001.

The invention claimed is:

1. A microneedle device, comprising:
    a) a cap having an upper surface and a lower surface;
    b) a backing having (i) an upper surface upon which abuts said lower surface of said cap, and (ii) a lower surface;
    c) a plurality of biodegradable microneedles having a length projecting from said lower surface of said backing and terminating in a tip distal from said lower surface of said backing, wherein said lower surface of said backing comprises a plurality of planar portions between said microneedles;
    d) wherein said microneedles comprise a polymeric blend of preserved stem cell factors; and
    e) a film coextensively covering said planar portions and said microneedles, wherein said film does not comprise bioactive agents and is formed from a flexible biocompatible material, whereupon applying said device to skin with pressure upon said cap, a length of said microneedles penetrates said film and the skin thereby positioning said microneedles in the skin, wherein said microneedles biodegrade and deliver said stem cell factors to the skin.

2. The device of claim 1, wherein said microneedles are configured to be positioned in the dermis.

3. The device of claim 1, wherein said microneedles are configured to be positioned in the epidermis.

4. The device of claim 1, wherein said film contacts said microneedles and said planar portions at an interface.

5. The device of claim 1, wherein said microneedles and said film are different materials.

6. A microneedle device, comprising:
    a) a cap having an upper surface and a lower surface;
    b) a backing having (i) an upper surface upon which abuts said lower surface of said cap, and (ii) a lower surface;
    c) a plurality of biodegradable microneedles having a length projecting from said lower surface of said backing and terminating in a tip distal from said lower surface of said backing, wherein said lower surface of said backing comprises a plurality of planar portions between said microneedles;
    d) said microneedles comprising a polymeric blend which comprises one or more therapeutic agents selected from the group consisting of a preserved stem cell composition, a preserved stem cell derivative, preserved biomolecules, and one or more active pharmaceutical ingredients; and
    e) a film coextensively covering said planar portions and said microneedles, wherein said film does not comprise active pharmaceutical ingredients and is formed from a flexible biocompatible material, whereupon applying said device to skin with pressure upon said cap, a length of said microneedles penetrates said film and the skin thereby positioning said microneedles in the skin, wherein said microneedles biodegrade and deliver said therapeutic agents to the skin.

7. The device of claim 6, wherein said active pharmaceutical ingredient is selected from one or more of minoxidil, botulinum toxin, and retinoic acid.

8. The device of claim 6, wherein said microneedles are configured to be positioned in the dermis.

9. The device of claim 6, wherein said microneedles are configured to be positioned in the epidermis.

10. The device of claim 6, wherein said film contacts said microneedles and said planar portions at an interface.

11. The device of claim 6, wherein said microneedles and said film are different materials.

* * * * *